United States Patent

Picha et al.

[11] Patent Number: 5,343,874
[45] Date of Patent: Sep. 6, 1994

[54] TRACT MEASURING DEVICE

[75] Inventors: George J. Picha, Independence; Dean J. Secrest, Concord; Angela P. Nguyen, Sagamore Hills, all of Ohio

[73] Assignee: Applied Medical Technology, Inc., Independence, Ohio

[21] Appl. No.: 63,118

[22] Filed: May 18, 1993

Related U.S. Application Data

[63] Continuation of Ser. No. 767,124, Sep. 27, 1991, abandoned.

[51] Int. Cl.$^5$ ............................................. A61B 5/103
[52] U.S. Cl. .................................. 128/780; 128/774; 604/264
[58] Field of Search ............... 604/8, 117, 164, 174, 604/175, 264, 280; 128/774, 780; 33/511, 512, 700

[56]  References Cited

U.S. PATENT DOCUMENTS

| 4,500,313 | 2/1985 | Young | 128/774 |
|---|---|---|---|
| 4,612,939 | 9/1986 | Robertson | 128/774 |
| 4,685,904 | 8/1987 | Krebs | 604/239 |
| 4,762,519 | 8/1988 | Frimberger | 604/164 |
| 4,826,481 | 5/1989 | Sacks et al. | 604/164 |
| 4,972,845 | 11/1990 | Iverson et al. | 128/774 |
| 4,981,470 | 1/1991 | Bombeck | 128/780 |
| 5,078,743 | 1/1992 | Mikalov et al. | 606/108 |
| 5,112,310 | 5/1992 | Grobe | 604/175 |

FOREIGN PATENT DOCUMENTS

| 0164398 | 8/1964 | U.S.S.R. | 128/780 |
|---|---|---|---|
| 0305884 | 6/1971 | U.S.S.R. | 604/117 |
| 9105577 | 5/1991 | World Int. Prop. O. | 604/117 |

Primary Examiner—John D. Yasko
Assistant Examiner—Anthony Gutowski
Attorney, Agent, or Firm—Pearne, Gordon, McCoy & Granger

[57]   ABSTRACT

A measuring device and method for determining the length of an incised tract or passage into which gastrostomy appliance is about to be installed. A trocar needle is used to incise a tract or passage extending from the outside surface of a patient's skin into the stomach through the abdominal and stomach walls. The measuring device is positioned in the patient's stomach via a previously endoscopically installed guidewire extending through the patient's mouth, down the esophagus and through the incision. The device is pushed along the guidewire outwardly through the incision until a distal end of the device containing scale indicia is visible. A stop on the device engages the inner wall of the patient's stomach to limit outward movement of the device through the incision, so as to establish an inner stomach wall reference point for the scale indicia. With the device fully inserted into the incision, the distance between the inner wall of t, he patient's stomach and the outer surface of the skin is measured by observation of the scale indicia. The measuring device is removed from the tract or passage, and then a gastrostomy appliance of proper length dimension determined by the foregoing measurement is installed.

18 Claims, 3 Drawing Sheets

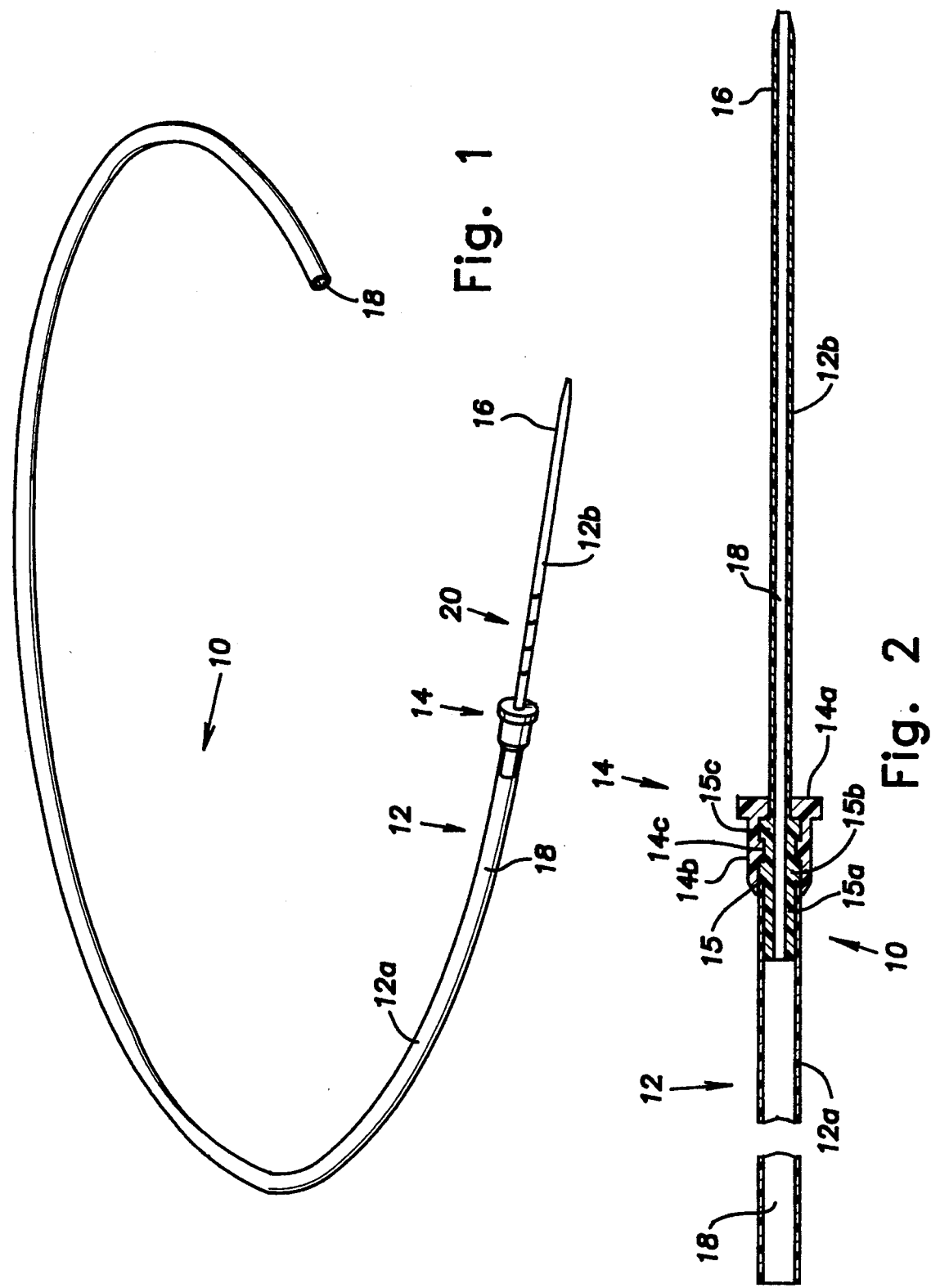

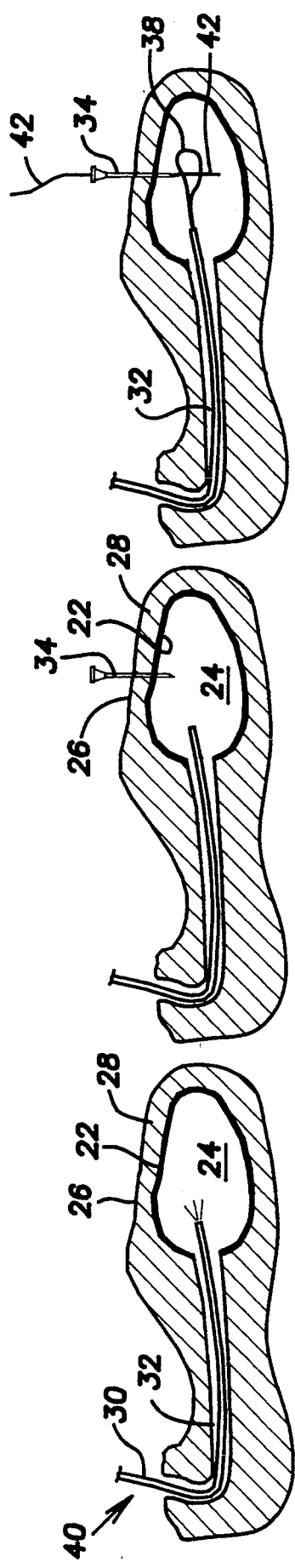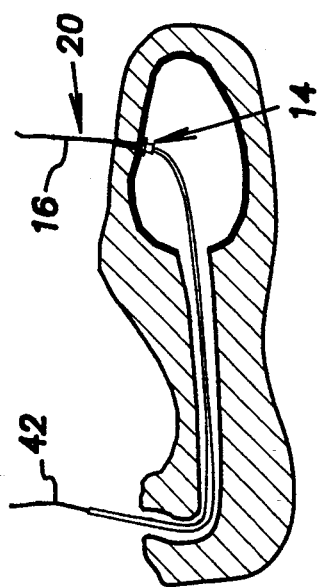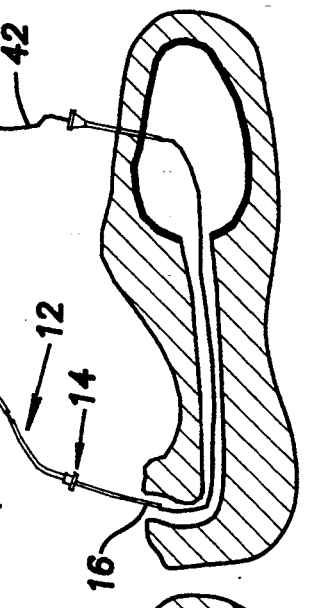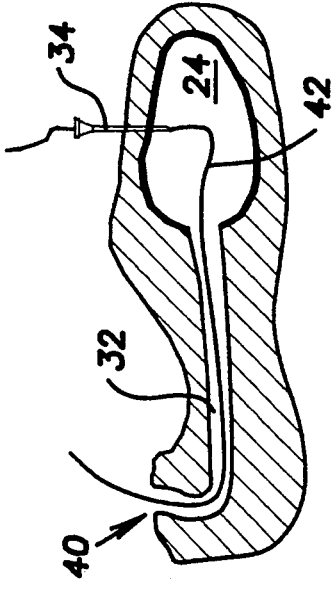

TRACT MEASURING DEVICE

This is a continuation of application Ser. No. 07/767,124, filed Sep. 27, 1991.

BACKGROUND OF THE INVENTION

The present invention relates in general to gastrostomies providing long term enteral feeding, and more particularly to a device and method for measuring the length of a tract or passage from a viscera to the skin, for example, the placement of a low profile gastrostomy appliance.

U.S. Pat. No. 5,084,014, owned by the assignee of the present invention and incorporated herein by reference, discloses an installation package and method for placing a low profile gastrostomy appliance into an incised tract or passage extending between the outer surface of a patient's skin and the inner wall of the patient's stomach. Low profile gastrostomy appliances are well known in the art as evidenced by U.S. Pat. No. 4,863,438, also owned by the assignee of the present invention and incorporated herein by reference.

The length of the tract or passage into which the gastrostomy appliance will be installed will vary from patient to patient. Therefore, in order to properly size an appliance to fit the recipient patient it is necessary to determine the length of the tract or passage. Variations in tract or passage length are due primarily to differences in the abdominal wall thickness between the patient's skin and stomach wall. A patient's age, sex and weight are key factors affecting wall thickness. Once the length of the tract or passage has been measured, an appropriately sized gastrostomy device of the low profile type or another type feeding device can be selected and.. then installed in the tract or passage, A device for providing the above-noted tract or passage length measurement should be simple to use, low in cost and preferably disposable. The associated method should be time efficient and should minimize the trauma caused to the patient.

SUMMARY OF THE INVENTION

The present invention provides a measuring device and method for determining the length of an incised tract or passage extending between the outer surface of a living body and an inner wall of an internal body cavity. Such a device and method are used, for example, to properly size a gastrostomy appliance or the like for subsequent installation in a recipient patient, Tract or passage lengths vary from patient to patient due to differences in abdominal wall thickness between the exterior skin and the inner stomach wall. Whereas factors such as age, sex, and weight could be used to estimate the tract or passage length, the present invention provides a much more accurate means of measurement. Without the present invention, physicians might have to remove and re-install different sized gastrostomy appliances or the like until a proper fit is obtained. Each time a gastrostomy appliance is removed and a new one installed, the patient faces an increased risk of trauma, perforation, and irritation of the mucosal lining of the digestive tract. The present invention offers a simple, inexpensive and safe technique for proper gastrostomy appliance selection.

The preferred embodiment of the device includes a fixed stop means and an elongated flexible tubular member. The elongated tubular member has a reduced diameter tapered distal end portion. Scale indicia is located on the flexible tubular member intermediate the distal end of the elongated tubular member and the stop means, with the stop means being located at one end of the scale indicia. The stop means includes a disc shaped stop surface, the center point of which lies along the longitudinal axis of the elongated member and is generally perpendicular thereto. The stop surface of the stop member is dimensionally sized to prevent passage of the stop member through the incised tract or passage.

In accordance with a preferred embodiment of the present invention, the elongated member is formed with a longitudinal bore extending along its entire length. The bore is sufficiently large to permit the elongated member to travel along a previously installed guidewire. The guidewire extends from just outside the patient's mouth, down the esophagus, into the patient's stomach and into and through an incised tract or passage. The incised tract or passage, which extends through the patient's stomach wall, across the abdominal wall, and through the exterior abdominal skin, is made previously with an appropriate instrument, such as a trocar needle.

Further in accordance with the present invention, the device is designed to be manipulated along a previously installed guidewire, allowing insertion of the distal end of the elongated member into and through the previously made incised tract or passage. The device is pushed downward until the stop means engages and is positioned against the inner stomach wall, enabling the distal end to extend out beyond the tract or passage. The tract or passage cross section is dimensioned to allow the distal end of the measuring device to pass therethrough while preventing the stop means, which is positioned against and in engagement with the inner cavity wall, from passing through the incised tract or passage.

When the distal end protrudes beyond the tract or passage, a physician need only gently pull the distal end to be assured that the stop means is positioned against the inner stomach wall. With the stop means securely engaging the stomach wall, the scale indicia are visible and facilitate an accurate determination of the length of the tract or passage.

The information regarding the tract or passage length derived from the device and method of the present invention provides the physician with the correct length for a gastrostomy appliance, or the like, for each patient. The preferred embodiment further provides a method for removing the device from the incised tract or passage and replacing it with a gastrostomy appliance or the like of suitable length dimension as determined by the measurement reading.

BRIEF DESCRIPTION OF THE DRAWINGS

A more complete understanding of the invention may be had by referring to the following description and claims, taken in conjunction with the accompanying drawings, wherein:

FIG. 1 is a perspective view of the measuring device of the present invention;

FIG. 2 is an elevational, cross-sectional view of the measuring device of FIG. 1 with portions cutaway;

FIGS. 3A–3F sequentially illustrate the methodology for placing the measuring device into and through an incised tract or passage in a human being;

DETAILED DESCRIPTION OF THE PREFERRED EMBODIMENT

Figure 4:
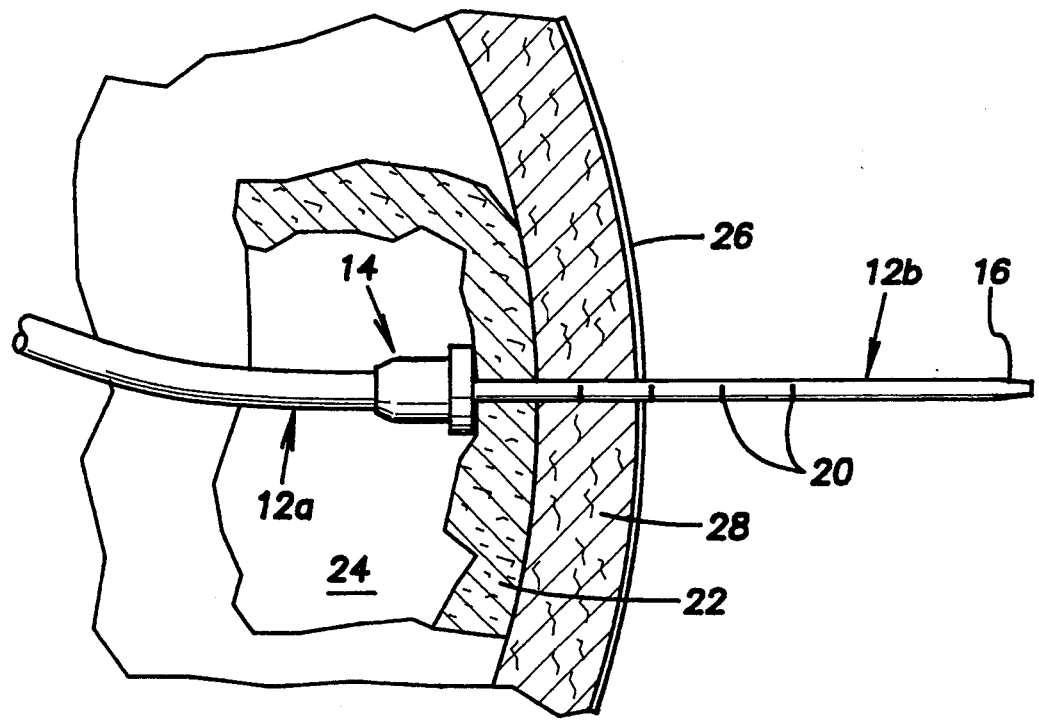
FIG. 4 provides an elevational view of the measuring device fully inserted into the incised tract or passage, with the stomach wall, abdominal wall, and skin shown in cross-section; and, FIG. 5 provides a side view of a correctly sized gastrostomy device installed in the incised tract or passage with the stomach wall, abdominal wall, and skin shown in cross-section.

FIGS 1 and 2 depict a preferred embodiment of a measuring device 10. The measuring device 10 is elongated and extends along a longitudinal axis as seen in FIG. 2. The measuring device 10 includes an elongated tubular member 12 and a stop means 14. The elongated member 12 includes a large diameter portion 12a and a reduced diameter portion 12b.

The elongated member 12 is formed of flexible elastomeric materials, for example thermoplastic elastomers (T.E.). The elongated member 12 includes a longitudinal bore 18 to allow the measuring device 10 to be manipulated into place along a guidewire 42, as ill be hereafter described with reference to FIGS. 3A-3F. The reduced diameter portion 12b has a tapered distal end 16 to ease passage through the incised tract or passage and includes the longitudinal bore 18 extending along its entire length.

The proximal end 15 of the reduced diameter portion includes a larger diameter segment 15a, and first, and second raised annular members 15b, 15c. The larger diameter segment 15a is dimensioned and sized to tightly fit within the tubular opening or bore 18 provided by the large diameter portion 12a, providing a mechanical bond between the large and reduced diameter portions 12a, 12b. The terminal edge of the large diameter portion 12a abuts the first raised annular member 15b provided on the reduced diameter portion 12b. In addition to forming a stop surface for the large diameter portion 12a, the first raised annular member 15b cooperates with the second raised annular member 15c to provide a seat to mechanically engage and hold the stop means 14, as will hereafter be described.

With further reference to FIGS. 1 and 2, along a portion of the outside of the elongated member 12 scale indicia 20 are marked to gauge the incised tract or passage length. The indicia are preferably in millimeter increments, but can be in any scale which indicates the wall thickness so that an appropriately-sized gastrostomy appliance may be selected. The scale indicia 20 lie between the tapered distal end 16 and the stop means 14 wherein the stop means 14, and more specifically, a generally planar stop surface 14a, represent the origin or reference point of the measurement.

The elongated member 12 is secured in place within the patient through use of the stop member 14. The stop member 14 includes the generally planar stop surface 14a and a connector portion 14b. Preferably, the stop surface 14a is disc shaped, with its center point lying along the longitudinal axis of the tubular member 12 and is generally perpendicular thereto. The connector portion 14b is generally cylindrical, and is mechanically connected to the reduced diameter portion 12b of the elongated member 12.

The stop member 14 and, more particularly, the stop surface 14a are sized so as to preclude the passage of the stop member 14 through the incised tract or passage. The stop surface 14a is dimensioned so that it cannot pass through the tract when it is manipulated into engagement with the inner stomach wall 22 or when a physician pulls on the reduced diameter portion 12b to confirm that the stop surface 14a is engaging the stomach wall 22.

To insure an accurate determination of the tract length, the aforementioned connector portion 14b is mechanically joined to the reduced diameter portion 12b. The connector portion 14b is provided with an inner O-shaped ring or seal 14c which is dimensioned and sized to snugly fit between the first and second raised annular members 15b, 15c provided by the proximal end 15 of the reduced diameter portion 12b. Additionally, the rear side of the stop surface 14a is in contact with the second raised annular member 15c to preclude relative longitudinal movement of the stop member 14 when the stop surface 14a is forced against the stomach wall 22 adjacent the tract or passage.

With the seal 14c of the connector portion 14b of the stop member 14 in place between the raised annular members 15b, 15c, the stop surface 14a in contact with the second raised annular member 15c, and the terminal end of the large diameter portion 12a engaging the first raised annular member 15b, the stop surface 14a provides a stable bearing surface for accurate measurement of the tract or passage length. When the stop surface 14a is in engagement with the inner stomach wall 22, the connector portion 14b and, more particularly, the engagement of the inner O-shaped ring 14c between the first end second raised annular members 15b, 15c and the engagement of the rear of the stop surface 14a with the second raised annular member 15c supports the stop member 14 and prevents the stop member from sliding down the large diameter portion 12a.

The two parts of the stop member 14, the stop surface 14a and connector portion 14b, work in unison to assure accurate measurement of tract length. Preferably, unified performance is accomplished by forming the stop member 14 as a single piece of elastomeric material. Naturally, it is possible to form the stop member out of two or more pieces which will attain the desired result.

FIGS. 3A-3F illustrate the method for installing the present device into a human patient. FIG. 3A schematically illustrates a patient having an inner body cavity such as a stomach 24 through which the measuring device 10 is passed through in accordance with the present invention.

The first step, FIG. 3A, for installing the measuring device 10 requires insufflation of the stomach 24 by means of an endoscope tube 30 so that the stomach wall is held tightly against the abdominal wall 28. The endoscope tube 30 is placed in the patient's mouth 40 and is manipulated down the patient's esophagus 32. In FIG. 3B, a trocar needle 34 is inserted through the abdominal wall 28 and stomach wall 22 of the patient to establish an incised tract or passage that extends from the outer surface of the abdominal wall 28, i.e. the skin 26, and into the stomach 24. It is within this incised tract or passage that the measuring device 10 will be inserted.

As depicted in FIG. 3C, a guidewire 42 is fed through the trocar needle 34 and retrieved by a snare 38, and the endoscope tube 30 with guidewire 42 is withdrawn from the esophagus 32. As shown in FIG. 3D, the guidewire 42 extends from outside the trocar needle 34, through the patient's stomach 24 and esophagus 32, and out the patient's mouth 40.

Turning to FIG. 3E, the measuring device 10 is threaded over the guidewire 42 using the longitudinal bore 18. The measuring device 10 is then manipulated along the guidewire 42 through the patient's mouth 40 and esophagus 32 until the distal end 16 is pushed outwardly through the incised tract or passage made by the trocar needle 34. In FIG. 3F the stop member 14 is resting against the stomach wall 22 and the scale indicia portion 20 of the reduced diameter portion 12b that extends beyond the outer skin 26 is visible to the attending physician.

FIG. 4 illustrates a determination of tract or passage length with the measuring device 10 using the scale indicia 20. The reading on the scale indicia is then used to select a properly-sized gastrostomy appliance 50. FIG. 4 further provides an enlarged cross-sectional view of the stomach 24, stomach wall 22, abdominal wall 28, skin 26 and measuring device 10. The reduced diameter portion 12b of the tubular member 12 is within the incised tract or passage previously made by the trocar needle. The stop surface 14a is in engagement with the stomach wall 22 and the reduced diameter portion 12b is positioned within and extends through the abdominal wall 28 and skin 26 to allow for easy reading of the scale indicia 20.

Figure 5:
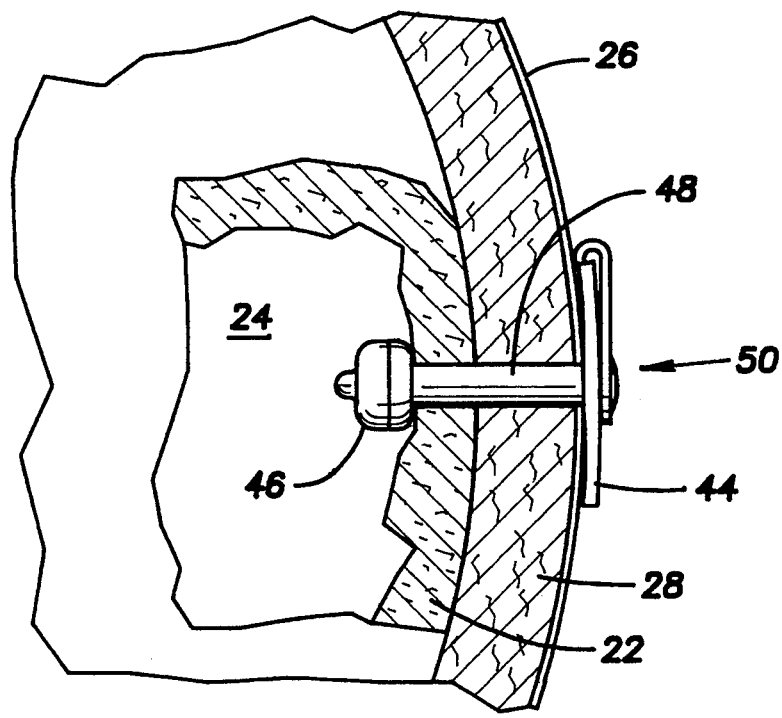

FIG. 5 shows a correctly sized gastrostomy appliance 50 installed following use of the measuring device 10 as described above with reference to FIG. 4. The gastrostomy appliance's wing-like projections 44 engage the outer surface or skin 26 of the patient, the tubular midportion 48 extends through the abdominal wall 28 of the patient, and the intragastric portion 46 is retained in the desired position within the patient's stomach 24.

It should be evident that this disclosure is by way of example, and that various changes may be made by adding, modifying or eliminating details without departing from the fair scope of the teaching contained in this disclosure. For example, it is within the scope of the present invention to form the stop means 14 integral the reduced diameter portion 12b of the elongated member. Therefore, it should be clear that the scope of the present invention is not limited to the particular configurations and details contained in the disclosure, but rather is to be defined by the appended claims.

What is claimed is:

1. A device for measuring an incised tract or passage extending between an outer surface of a living body and an inner wall of an internal body cavity, said device comprising:

an elongated tubular member comprising a relatively reduced diameter portion and an elongated relatively enlarged diameter portion, said enlarged diameter portion being larger than said reduced diameter portion, said portions cooperating to define a lengthwise extending bore, said reduced diameter portion having visible scale indicia along at least a portion of its length, a proximal end of the reduced diameter portion being received by and attached to a distal end of the enlarged diameter portion, a distal end of the reduced diameter portion and a proximal end of the enlarged diameter portion having openings therethrough in communication with the bore; and a stop member, said stop member interconnecting the enlarged and reduced diameter portions and providing a stop surface which defines a reference point for said visible scale indicia, said visible scale indicia being located between a distal end of said reduced diameter portion and said stop member, said stop member being of fixed dimensions to preclude its passage through said incised tract, wherein said device, when located in said body cavity, is adapted to be manipulated so as to insert the distal end of the reduced diameter portion into and through said incised tract to a position wherein said scale indicia is visible from outside said body when the stop surface provided by the stop member engages and is positioned against said inner wall, said scale indicia being readable from outside said body so as to determine the length of said incised tract.

2. A device according to claim 1 wherein said lengthwise extending bore is adapted to receive and slide along a guidewire, said guidewire extending completely through said incised tract or passage.

3. A device according to claim 1 wherein said tubular member is formed of flexible elastomeric material.

4. A device according to claim 1 wherein said scale indicia is constituted by a series of scale markings indicative of a length of the reduced diameter portion along which the scale indicia extends, said length corresponding to the length of the incised tract or passage extending between the outer surface of the living body and the inner wall of the internal body cavity.

5. A device according to claim 4 wherein said scale markings are in millimeter increments.

6. A device according to claim 1 wherein the distal end of the reduced diameter portion is tapered.

7. A device according to claim 1 wherein said tubular member is formed of thermoplastic elastomers (T.E.).

8. A device for measuring an incised tract or passage extending between an outer surface of a living body and an inner wall of an internal body cavity, said device comprising:

an elongated flexible tubular member, said tubular member defining a longitudinal bore open at proximal and distal ends of the tubular member and adapted to slidably receive a guidewire and comprising proximal and distal members, said distal member having a smaller diameter than the proximal member and including scale indicia, said proximal member being longer than said distal member;

means for connecting the proximal member to the distal member;

means for limiting the passage of said tubular member through the incised tract or passage, wherein said device, when located in said body cavity, is adapted to be manipulated to insert a terminal end of said distal member into and through said incised tract or passage to a position wherein the scale indicia is visible from outside said body when said limiting means engages and is positioned against said inner wall, said scale indicia being readable from outside said body to determine the length of the incised tract or passage.

9. A device according to claim 8 wherein said limiting means comprises an annular surface, said annular surface being generally coaxial with the elongated tubular member.

10. A method of measuring the length of an incised tract or passage extending between an outer surface of a living body and an inner wall of an internal body cavity, comprising the steps of:

providing a measuring device comprising an elongated member having an elongated relatively enlarged diameter portion with a proximal end; a relatively reduced diameter portion with a distal end; and a stop surface disposed between said portions, said enlarged diameter portion being longer than said reduced diameter portion, said member having visible scale indicia along at least a portion of its length;

positioning said device within said body cavity;

applying a pushing force on said proximal end and manipulating said distal end into and through said incised tract or passage to a position wherein said stop surface engages the inner wall and the scale indicia is visible from outside said body; and reading said scale indicia from outside the body to determine the length of the incised tract or passage.

11. A method according to claim 10 including the step of removing said device from said incised tract or passage and installing in its place a gastrostomy appliance or the like of suitable length dimension ad determined by said measurement.

12. A method of measuring an incised tract or passage as recited in claim 10, wherein said step of providing a measuring device further comprises said scale indicia being provided between the stop surface and the distal end of the elongated member.

13. A method of measuring an incised tract or passage according to claim 10, wherein said elongated member defines a longitudinal bore and said positioning step includes:

providing a guidewire which extends through an external orifice, into said internal body cavity, and through said incised tract;

sliding the guidewire through the longitudinal bore; and pushing said device along said guidewire, through said external orifice, and into said internal body cavity.

14. A method of measuring an incised tract or passage according to claim 10, wherein the manipulating step includes the step of pushing said device along a guidewire and through the incised tract.

15. A method of measuring an incised tract or passage as recited in claim 14, wherein said step of providing a measuring device further comprises the scale indicia being provided between the distal end and the stop surface, said stop surface defining a reference point for said scale indicia.

16. A method of measuring an incised tract or passage as recited in claim 10, wherein said step of providing a measuring device further comprises the elongated member comprising first and second members which cooperate to define a longitudinal bore, said stop surface being provided by a stop member which interconnects the first and second members.

17. A method of measuring an incised tract or passage as recited in claim 16, wherein said step of providing a measuring device further comprises the first member having a smaller diameter than the second member and provides the distal end, said scale indicia being provided along the first member.

18. A method of measuring an incised tract or passage as recited in claim 17, wherein said positioning step includes the steps of:

providing a guidewire which extends through an external orifice, into said internal body cavity, and through said incised tract;

sliding the guidewire through the longitudinal bore; and pushing said device along said guidewire, through said external orifice, and into said internal body cavity.

* * * * *

UNITED STATES PATENT AND TRADEMARK OFFICE
CERTIFICATE OF CORRECTION

PATENT NO. : 5,343,874

DATED : September 6, 1994

INVENTOR(S) : Picha et al.

It is certified that error appears in the above-identified patent and that said Letters Patent is hereby corrected as shown below:

```
On the face of the patent, in the abstract, line 2, after
    "which" insert --a--;
    line 18, delete "t, he" and insert --the--; and
    line 22, after "dimension" insert --as--.

Column 1, line 36, delete "and.." and insert --and--; and
    line 50, delete "patient," and insert --patient.--.

Column 3, line 27, delete "ill" and insert --will--; and
    line 28, after "first" delete "," (comma).

Column 7, line 14, (Claim 11, line 4), delete "ad" and
    insert --as--.
```

Signed and Sealed this

Twenty-fourth Day of January, 1995

*Attest:*

BRUCE LEHMAN

*Attesting Officer*     *Commissioner of Patents and Trademarks*